United States Patent [19]

Morton, Jr.

[11] 4,275,197

[45] Jun. 23, 1981

[54] 9,11-DIDEOXY-10-OXA-TXB INTERMEDIATES

[75] Inventor: Douglas R. Morton, Jr., Portage, Mich.

[73] Assignee: The Upjohn Company, Kalamazoo, Mich.

[21] Appl. No.: 116,324

[22] Filed: Jan. 28, 1980

Related U.S. Application Data

[62] Division of Ser. No. 19,752, Mar. 12, 1979.

[51] Int. Cl.$^3$ ..................... C07D 319/06; C07D 5/12
[52] U.S. Cl. ................................. 542/413; 260/340.7; 542/427; 542/438
[58] Field of Search .................... 260/340.7; 542/427, 542/413, 438

[56] References Cited

U.S. PATENT DOCUMENTS 3,950,353  4/1976  Bundy ............................... 260/347.3
4,070,384  1/1978  Schneider ........................... 260/406

OTHER PUBLICATIONS

Lourens et al., Tet Let. 1957, pp. 3715–3718.

*Primary Examiner*—Arthur P. Demers
*Attorney, Agent, or Firm*—Robert A. Armitage

[57] ABSTRACT

The present invention relates to novel compositions of matter and particularly provides 9,11-dideoxy-10-oxa-TXB intermediates for preparing corresponding thromboxane analogs. These thromboxane analogs are useful for a variety of pharmacologically useful purposes, most particularly as anti-thrombotic agents.

1 Claim, No Drawings

9,11-DIDEOXY-10-OXA-TXB INTERMEDIATES

CROSS REFERENCE TO RELATED APPLICATION

The present application is a divisional application of U.S. Ser. No. 019,752, filed Mar. 12, 1979, now pending issuance as a United States patent.

DESCRIPTION

Background of the Invention

The present invention relates to novel compositions of matter the preparation and use of which is incorporated here by reference from U.S. Ser. No. 019,752. Particularly the present invention provides novel analogs of the thromboxanes. Most particularly, the present invention specifically relates to novel 9,11-dideoxy-10-oxa-TXB intermediates for preparing corresponding thromboxanes.

PRIOR ART

Thromboxane $B_2$ is known in the art. See Samuelsson, Proceedings of the National Academy of Sciences USA 71:3400–3404 (1974). Likewise, numerous analogs of thromboxane $B_2$ and their use as reproductive cycle control agents is known in the art. See U.S. Pat. No. 4,070,384, issued Jan. 24, 1978.

Further, certain 11-oxa prostaglandin-type compounds are known in the art. See particularly Belgian Pat. No. 830,423 (Derwent Farmdoc CPI No. 01971X) and Tetrahedron Letters 43:3715–3718 (1975).

Other heterocyclic ring analogs of the prostaglandins include the $9\alpha,11\alpha$- or $11\alpha,9\alpha$-epoxymethano-9,11-dideoxy-PGF-type compounds described in U.S. Pat. Nos. 3,950,363 and 4,028,354. Finally related azo and epoxyimino compounds are known in the art. See U.S. Pat. No. 4,112,224.

SUMMARY OF THE INVENTION

The present invention particularly provides
A thromboxane intermedate of formula IV, V, VI, or VII

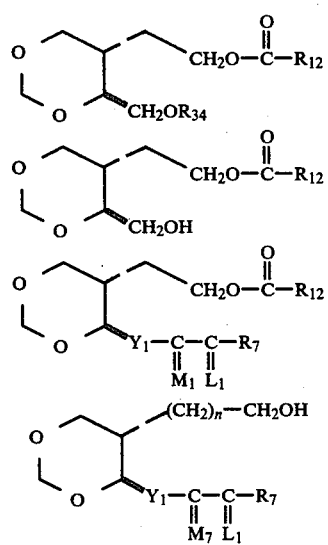

wherein $Y_1$ is
(1) trans—CH=CH—,
(2) cis—CH=CH—,
(3) —CH$_2$CH$_2$—, or
(4) —C≡C—,
wherein $M_1$ is $\alpha$—$R_5$:$\beta$—OH, $\alpha$—OH:$\beta$—$R_5$, or $\alpha$—H:$\beta$-H, wherein $R_5$ is hydrogen or methyl;
wherein $L_1$ is $\alpha$—$R_3$:$\beta$—$R_4$, $\alpha$—$R_4$:$\beta$—$R_3$, or a mixture of $\alpha$—$R_3$:$\beta$—$R_4$ and $\beta$—$R_3$:$\alpha$—$R_4$, wherein $R_3$ and $R_4$ are hydrogen, methyl, or fluoro, being the same or different, with proviso that one of $R_3$ and $R_4$ is fluoro only when the other is hydrogen or fluoro;
wherein g is one, 2, or 3;
wherein $R_7$ is
(1) —(CH$_2$)$_m$—CH$_3$, wherein m is an integer from one to 5 inclusive;
(2) phenoxy;
(3) phenoxy substituted by one, two, or three chloro, fluoro, trifluoromethyl, alkyl of one to 3 carbon atoms, icnlusive, or alkoxy of one to 3 carbon atoms, inclusive, with the proviso that not more than two substituents are other than alkyl;
(4) phenyl;
(5) phenyl substituted by one, two, or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two, or three chloro, fluoro, trifluoromethyl, alkyl of one to 3 carbon atoms, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $M_7$ is $\alpha$—$R_5$:$\beta$—$OR_{10}$, $\alpha$—$OR_{10}$:$\beta$—$R_5$, or $\alpha$—H:$\beta$—H, wherein $R_{10}$ is a stable, acid hydrolyzable blocking group;
wherein $R_{12}$ is alkyl of one to 12 carbon atoms, inclusive, aralkyl of 7 to 12 carbon atoms, inclusive, aralkyl of 7 to 12 carbon atoms, inclusive; phenyl; or phenyl substituted with one, 2 or 3 chloro or alkyl of one to 3 carbon atoms, and
wherein $R_{34}$ is a stable, hydrogenolyzable blocking group.

I claim:
1. A thromboxane intermediate of formula IV, V, VI, or VII

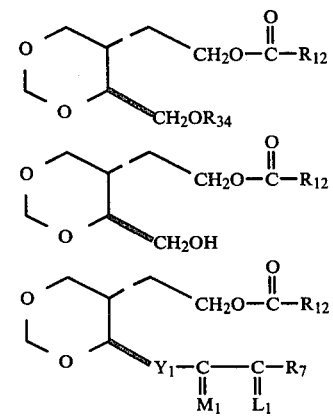

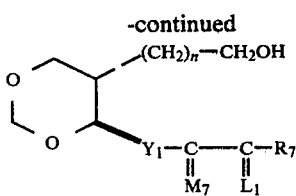

VII wherein $Y_1$ is
(1) trans—CH=CH—,
(2) cis—CH=CH—,
(3) —CH$_2$CH$_2$—, or
(4) —C≡C—,
wherein $M_1$ is $\alpha$—$R_5$:$\beta$—OH, $\alpha$—OH:$\beta$—$R_5$, or $\alpha$—H:$\beta$—H, wherein $R_5$ is hydrogen or methyl;
wherein $L_1$ is $\alpha$—$R_3$:$\beta$—$R_4$, $\alpha$—$R_4$:$\beta$—$R_3$, or a mixture of $\alpha$—$R_3$:$\beta$—$R_4$ and $\beta$—$R_3$:$\alpha$—$R_4$, wherein $R_3$ and $R_4$ are hydrogen, methyl, or fluoro, being the same or different, with proviso that one of $R_3$ and $R_4$ is fluoro only when the other is hydrogen or fluoro;
wherein g is one, 2, or 3;
wherein $R_7$ is
(1) —(CH$_2$)$_m$—CH$_3$, wherein m is an integer from one to 5 inclusive;
(2) phenoxy;
(3) phenoxy substituted by one, two, or three chloro, fluoro, trifluoromethyl, alkyl of one to 3 carbon atoms, icnlusive, or alkoxy of one to 3 carbon atoms, inclusive, with the proviso that not more than two substituents are other than alkyl;
(4) phenyl;
(5) phenyl substituted by one, two, or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two, or three chloro, fluoro, trifluoromethyl, alkyl of one to 3 carbon atoms, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $M_7$ is $\alpha$—$R_5$:$\beta$—$OR_{10}$, $\alpha$—$OR_{10}$:$\beta$—$R_5$, or $\alpha$—H:$\beta$—H, wherein $R_{10}$ is a stable, acid hydrolyzable blocking group;
wherein $R_{12}$ is alkyl of one to 12 carbon atoms, inclusive, aralkyl of 7 to 12 carbon atoms, inclusive, aralkyl of 7 to 12 carbon atoms, inclusive; phenyl; or phenyl substituted with one, 2 or 3 chloro or alkyl of one to 3 carbon atoms, and
wherein $R_{34}$ is a stable, hydrogenolyzable blocking group.

* * * * *

UNITED STATES PATENT OFFICE
CERTIFICATE OF CORRECTION

Patent No. 4,275,197     Dated 23 June 1981

Inventor(s) Douglas R. Morton, Jr.

It is certified that error appears in the above-identified patent and that said Letters Patent are hereby corrected as shown below:

Column 1, lines 7-8, "now pending issuance as a United States patent" should read -- now U.S. Patent 4,243,592 --; line 15, "U.S. Ser. No. 019,752" should read -- U.S. Patent 4,243,592 --;

Column 2, line 12, and Column 3, line 23, "wherein g is one, 2, or 3," should read -- wherein n is one or two; wherein g is one, w, or 3, --;

Column 2, line 20, and Column 3, line 30, "icnlusive," should read -- inclusive --.

Signed and Sealed this

Sixth Day of October 1981

[SEAL]

Attest:

Attesting Officer

GERALD J. MOSSINGHOFF

Commissioner of Patents and Trademarks